United States Patent [19]

Westernacher

[11] 4,128,594

[45] Dec. 5, 1978

[54] PROCESS FOR THE PURIFICATION OF ALKYL AROMATICS

[75] Inventor: Helmut Westernacher, Haltern, Fed. Rep. of Germany

[73] Assignee: Chemische Werke Huels Aktiengesellschaft, Marl, Fed. Rep. of Germany

[21] Appl. No.: 897,606

[22] Filed: Apr. 18, 1978

Related U.S. Application Data

[63] Continuation-in-part of Ser. No. 760,714, Jan. 19, 1977, abandoned.

[30] Foreign Application Priority Data

Jan. 21, 1976 [DE] Fed. Rep. of Germany ....... 2602069

[51] Int. Cl.$^2$ ............................................... C07C 7/01
[52] U.S. Cl. ................................ 260/674 A; 208/262; 260/671 R; 260/671 P; 260/671 B; 260/674 R

[58] Field of Search ........... 260/674 R, 674 A, 671 R, 260/671 P, 671 B; 208/262

[56] References Cited

U.S. PATENT DOCUMENTS 3,679,770  7/1972  Nicolet ........................... 260/674 A

*Primary Examiner*—Delbert E. Gantz
*Assistant Examiner*—C. E. Spresser
*Attorney, Agent, or Firm*—Millen & White

[57] ABSTRACT

A process for the purification of crude alkylate from the Friedel-Crafts alkylation of aromatics comprises introducing anhydrous ammonia under anhydrous conditions into the crude alkylate
 (a) at a temperature of 40°–70° C, preferably 50°–60° C;
 (b) to a pH of 7–9, preferably 7.5–8.5; and
 (c) at a pressure of 0.4–25 bars, preferably 2–5 bars. During the introduction of ammonia, the crude alkylate can be agitated.

5 Claims, No Drawings

PROCESS FOR THE PURIFICATION OF ALKYL AROMATICS

CROSS REFERENCE TO RELATED APPLICATIONS

This application is a continuation-in-part of U.S. application Ser. No. 760,714 filed on Jan. 19, 1977, now abandoned.

BACKGROUND OF THE INVENTION

This invention relates to an anhydrous process for the purification of alkyl aromatics obtained by the Friedel-Crafts reaction of aromatics with olefins in the presence of an aluminum chloride catalyst and isolation following precipitation of the catalyst complex with anhydrous ammonia.

Alkyl aromatics are produced commercially on a large scale by the Friedel-Crafts reaction. For example, ethylbenzene is made from benzene and ethylene with aluminum chloride as catalyst and hydrogen chloride as promoter. The anhydrous crude alkylate obtained by this reaction still contains catalyst complex and hydrogen chloride, both of which must be removed prior to distillation of the product. This is accomplished in a separating tank wherein the bulk of the heavier catalyst complex is separated by phase separation. In the method of Russian Pat. No. 309,570 and DOS (German Unexamined Laid-Open application) No. 2,365,175, residual catalyst complex in the crude alkylate after phase separation is converted by reaction with ammonia to a compound insoluble in the crude alkylate and is then separated mechanically.

In the process of Russian Pat. No. 309,570, gaseous ammonia is introduced into crude alkylate at a temperature between 70° and 80° C. According to the example given in DOS No. 2,365,175, the aluminum compound is precipitated after being cooled to 60° C. This reference gives no data as to the quantity of ammonia utilized. In the example of Russian Pat. No. 309,570, ammonia is used in excess of 0.01-0.02 gram per liter of crude alkylate. The pH value is 9-10 in the aqueous extract of the crude alkylate. No data are given regarding pressure during ammonia addition in either Russian Pat. No. 309,570 or in DOS No. 2,365,175. Therefore, it is assumed that both processes are conducted at atmospheric pressure. The slightly soluble aluminum compounds formed under these conditions, i.e., a temperature of 60° to 70°-80° C, respectively, pH of 9-10 in the aqueous extract (required because these prior art processes are performed under anhydrous conditions), at a pressure of 0 bar, however, have the grave disadvantage of being difficult to filter. The filtration rate is very slow. A further disadvantage of the known techniques is that, when ammonia is introduced at atmospheric pressure, the formation of ammonium chloride in the gas space above the reaction mixture is uncontrollable. Since ammonium chloride is sublimed at high temperatures, it will be deposited in pipes and apparatus, with consequent clogging and marked reduction of the heat transfer capacity of the distillation columns after a short period of time.

Therefore, there is a continuing need for a process for removing residual catalyst complexes from Friedel-Crafts alkylate by addition of anhydrous ammonia under anhydrous conditions without incurring these disadvantages and to produce easily filterable precipitates but no uncontrolled deposition of $NH_4Cl$.

SUMMARY OF THE INVENTION

This invention relates, in a process for the purification of an impure alkyl aromatic compound, produced by a Friedel-Crafts reaction employing aluminum chloride reaction catalyst and a promoter, followed by phase separation to separate the major proportion of reaction catalyst, by neutralization under anhydous conditions, with ammonia of residual catalyst complex and hydrogen chloride present in the impure alkyl aromatic compound, to the improvement wherein the anhydrous neutralization with ammonia is conducted at a temperature of 40°–70° C, at pH of 7–9 and at a pressure of 0.5–25 bars.

DETAILED DESCRIPTION

The anhydrous crude alkylate being purified, for example, ethylbenzene or cumene or dibenzyltoluene crude alkylate is obtained by Friedel-Crafts reaction, under anhydrous conditions, of course, with $AlCl_3$ catalyst and HCl as promoter, from benzene or toluene and ethylene or propylene, respectively, or benzyl chloride, at a temperature of 70°–120° C and under a pressure of 1–2 bars.

Other alkyl aromatic compounds which can be treated by the method of this invention are diethylbenzene, triethylbenzene, diisopropylbenzene, triisopropylbenzene, di- and tri-propylbenzene, t-butyl-benzene, 2-phenyl-pentane, cyclohexylbenzene, p-chloroethylbenzene, diethyltoluene, n-butyltoluene and 5-isopropyl-m-xylene.

The catalyst for the reaction is preferably aluminum chloride, but other aluminum halides, especially aluminum bromide can be used. The limits for the acid number of the impure alkyl aromatic compound are 0.5 and 5.

A catalyst promoter, such as hydrogen chloride, hydrogen bromide and ethylchloride is used.

However, hydrogen chloride is preferred.

References to the Friedel-Crafts alkylation and subsequent isolation of the product include, in addition to those cited above, *Org. Reactions* III 1/76 [1945] and *Ullmanns Encyclopädie der technischen Chemie*, third Edition, 1956, Vol. 7, page 680 and pages following, Verlag Urban und Schwarzenberg, München-Berlin.

The temperature for purification of 40°–70° C, preferably 50°–60° C, is adjusted by cooling the crude alkylate.

The pH is measured in an aqueous extract of the crude alkylate and is maintained at 7–9 by controlled feeding of an amount of anhydrous ammonia of 10–1,000 ml/l of crude alkylate. In other words, since the neutralization system is anhydrous, pH measurement cannot be performed directly on the neutralization medium. Thus, as is conventional in cases such as these, e.g., see Russian Pat. No. 309,570 and DOS No. 2,365,175 mentioned above, an extract of the neutralization medium is taken and water is added thereto to form an aqueous extract in which conventional pH measurements can be taken. Usually, from 0.5–1 ml of $H_2O$ is added per one milliliter of neutralization medium extract.

The pressure of 0.5–25 bars, preferably 2–5 bars, is adjusted with a pump and maintained by a throttled valve, preferably in a system completely filled with liquid.

By combination of these three features, a precipitate which can be readily filtered is surprisingly obtained.

This has the advantage of keeping the filtering surface required low and the filtering operation is thus rendered economical.

Reaction with anhydrous ammonia at temperatures below 40° C and above 70° C impairs the filtering properties of the precipitate. Pressure and pH also affect the filtering capacity. An optimum filtering rate is attained if the precipitation with $NH_3$ is carried out at a temperature of 40°–60° C, most preferably 50° C, up to pH of 7.5–8.5 and under a pressure of 2–5 bars.

By control of the pH, for example, at 7–8, the amount of inorganic impurities in the filtrate can be kept at an extremely low value, for example, 2–3 p.p.m.

Precipitation with ammonia at pH values above 9 unexpectedly leads to a higher content of inorganic components in the filtrate.

The combination of conditions used according to the invention furthermore has the advantage of preventing deposition of ammonium chloride in pipelines and installations. Clogging is thereby avoided and heat transfer in distillation columns is not reduced.

The process of the invention eliminates the disadvantages hitherto observed during the anhydrous purification of alkyl aromatics with ammonia. The crude alkylate obtained according to this method can be distilled directly due to an extremely low content of inorganic impurities.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

The ethylbenzene crude is prepared according to the well known tower-process of the BASF (*Ullmanns Encyclopädie der technischen Chemie,* third Edition, 1956, Vol. 10, page 74 and pages following). As catalyst promoter hydrogen chloride B. W. Sherwood, Ind. Chemists 30, page 25 (1954)) is used. Into an alkylation-tower benzene, ethene and hydrogen chloride are introduced continuously in a parallel current at the bottom. The aluminum chloride catalyst is periodical added at the top. The reaction is exothermic. The temperature of 95°–96° C is maintained by metering benzene addition. 45–48% by weight of the benzene is unreacted. Ethene reacts completely. 0.5 to 0.7% by weight of $AlCl_3$ is added, based on the amount of hydrocarbons employed. The specific heavier catalyst complex is separated by phase separation. The crude alkylate with residual catalyst complex and hydrogen chloride is then purified by neutralization with ammonia.

The cumene crude is prepared in the manner of the preparation of ethylbenzene adding propene instead of ethene.

The dibenzyltoluene crude is prepared according to the procedure of example 3 in DT-AS No. 10 85 877. In a reaction vessel (10 l) 4340 g of toluene are continuously reacted at 110° C with 710 g of chlorine per hour. The overflow, a mixture of 3410 g of toluene and 1260 g of benzylchloride reacts in a second reaction vessel (10 l) with 3300 g of benzyltoluene per hour. As catalyst 22 g of $AlCl_3$ per hour are used. The temperature of the reaction is 60°–70° C. During the reaction about 300 g of hydrogen chloride are produced. The reaction mixture flows out of the top of the reaction vessel 2. The heavier aluminum chloride catalyst complex is separated by phase separation. The crude alkylate with residual catalyst complex and hydrogen chloride is then purified by neutralization with ammonia.

EXAMPLE 1

In a pressure vessel which can be heated and is equipped with an agitator, a thermometer and a manometer, anhydrous ammonia is introduced under anhydrous conditions into 1000 g of ethylbenzene crude alkylate having an acid number of about 1 due to catalyst complex entrained during the phase separation and excess hydrogen chloride. Temperatures of 20°, 40°, 50°, 70° and 100° C, pH values of 7, 8, 9 and 10 and pressures of 0, 1, 3, 5 and 15 bars, respectively, are used. (See Tables 1 through 4). The thus-obtained precipitate is separated at room temperature under a constant vacuum of 40–45 mm Hg on a porous filter plate 4.5 cm in diameter and provided with a black band filter. The filter cake on the porous plate is dried and weighed. The proportion of inorganic components in the filtrate is determined by quantitative analysis. The filtering period is used as a measure of the filtration rate and thus the filtering capacity of the precipitate.

Tables 1–4 show the results of the experimental series set forth in this example.

TABLE 1

Dependence of the Filtering Rate on the Temperature and pH Value Under Constant Pressure (Atmospheric Pressure)

| Temp. | Filtering Rate (Minutes) at | | | |
|---|---|---|---|---|
| ° C. | pH 7 | pH 8 | pH 9 | pH 10 |
| 20 | 32 | 19 | 17 | 27 |
| 40 | 24 | 17 | 14 | 21 |
| 50 | 17 | 11 | 12 | 16 |
| 70 | 19 | 14 | 17 | 23 |
| 100 | 28 | 17 | 18 | 25 |

TABLE 2

Dependence of the Filtering Rate on the Temperature and Pressure at a Constant pH Value (8)

| Temp. | Filtering Rate (Minutes) at | | | |
|---|---|---|---|---|
| ° C. | 0 bar | 1 bar | 5 bar | 15 bar |
| 20 | 19 | 17 | 16 | 21 |
| 40 | 17 | 15 | 14 | 19 |
| 50 | 11 | 9 | 7 | 13 |
| 70 | 14 | 10 | 7 | 14 |
| 100 | 17 | 13 | 12 | 23 |

TABLE 3

Dependence of the Content of Inorganic Components in the Filtrate on the pH Value

| Temp. | Inorganic Residue in p.p.m. | | |
|---|---|---|---|
| ° C. | pH 7 | pH 8 | pH 9 |
| 50 | 2 | 3 | 8 |

TABLE 4

Dependence of the Solids Obtained on Temperature and Pressure at a Constant pH Value (8)

| | Solid Matter g./1000 g. Crude Alkylate at | |
|---|---|---|
| Temp. ° C. | 0 bar | 3 bars |
| 20 | 1.05 | 1.20 |
| 40 | 1.01 | 1.23 |
| 50 | 0.99 | 1.22 |
| 70 | 0.86 | 1.20 |
| 100 | 0.58 | 1.21 |

The higher amounts of solids at 3 bars, uniformly over the entire temperature range, demonstrate that no uncontrolled deposits, for example, due to $NH_4Cl$ sublimation, occur in the apparatus.

EXAMPLE 2

In the manner of Example 1, anhydrous ammonia is introduced, under anhydrous conditions until the specified pH has been reached, into 1000 g of cumene crude alkylate having an acid number of about 2.5 due to entrained catalyst complex and to excess hydrogen chloride during the phase separation.

Results of the experiments of this example are compiled in Tables 5 and 6.

TABLE 5

Dependence of the Filtering Rate on the Temperature and pH Value Under Constant Pressure (Atmospheric Pressure)

| Temp. | Filtering Rate in Minutes at | | | |
| °C. | pH 7 | pH 8 | pH 9 | pH 10 |
| --- | --- | --- | --- | --- |
| 20 | 40 | 25 | 26 | 31 |
| 40 | 28 | 19 | 24 | 27 |
| 50 | 17 | 13 | 22 | 23 |
| 70 | 21 | 16 | 27 | 26 |
| 100 | 38 | 19 | 28 | 29 |

TABLE 6

Dependence of the Filtering Rate on the Temperature and Pressure at a Constant pH Value (8)

| Temp. | Filtering Rate in Minutes at | | | |
| °C. | 0 bar | 1 bar | 5 bar | 15 bar |
| --- | --- | --- | --- | --- |
| 20 | 25 | 23 | 21 | 29 |
| 40 | 19 | 13 | 11 | 21 |
| 50 | 13 | 8 | 6 | 10 |
| 70 | 16 | 10 | 9 | 15 |
| 100 | 19 | 17 | 16 | 23 |

EXAMPLE 3

In accordance with the disclosure of Example 1, anhydrous ammonia is introduced, under anhydrous conditions, until the desired pH value has been reached, into 1000 g of dibenzyltoluene crude alkylate having an acid number of 4.3 due to entrained catalyst complex and to excess hydrogen chloride.

The results of the series of experiments of this example are combined in Tables 7 and 8.

TABLE 7

Dependence of the Filtering Rate on the Temperature and pH Value Under Constant Pressure (Atmospheric Pressure)

| Temp. | Filtering Rate in Minutes at | | |
| °C. | pH 7 | pH 8 | pH 9 |
| --- | --- | --- | --- |
| 20 | 25 | 19 | 20 |
| 50 | 20 | 11 | 13 |
| 100 | 23 | 17 | 18 |

TABLE 8

Dependence of the Solids Obtained on Pressure and Temperature at a Constant pH Value (8)

| Temp. | Solid Matter g./1000 Crude Alkylate | |
| °C. | Atmospheric Pressure | 3 bars |
| --- | --- | --- |
| 20 | 3.5 | 3.8 |
| 60 | 3.0 | 3.9 |
| 100 | 1.8 | 3.7 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. In a process for the purification of an impure alkyl aromatic compound, produced by a Friedel-Crafts reaction employing aluminum chloride reaction catalyst and a promoter, by the successive steps of phase separation of the reaction product to separate therefrom the major proportion of reaction catalyst, neutralization with anhydrous ammonia of residual catalyst complex and hydrogen chloride present in the separated impure alkyl aromatic compound, and filtration of the neutralized product, the improvement wherein the neutralization with ammonia is conducted at a temperature of 40°–70° C at pH of 7–9 and at a pressure of 0.5–25 bars.

2. The process of claim 1, wherein the neutralization is conducted at a temperature of 50°–60° C at a pH of 7.5–8.5 and at a pressure of 2–5 bars.

3. The process of claim 1, wherein the promoter is hydrogen chloride.

4. The process of claim 1, wherein stirring is maintained during ammonia addition.

5. The process of claim 1, wherein the alkyl aromatic compound is ethylbenzene, cumene or dibenzyltoluene.

* * * * *